United States Patent
Kuriyama et al.

(10) Patent No.: US 10,359,411 B2
(45) Date of Patent: Jul. 23, 2019

(54) DIAGNOSIS METHOD FOR INTERNAL FAULT OF OIL-IMMERSED ELECTRIC APPARATUS

(71) Applicant: Mitsubishi Electric Corporation, Chiyoda-ku, Tokyo (JP)

(72) Inventors: Ryota Kuriyama, Tokyo (JP); Fukutaro Kato, Tokyo (JP); Shiki Hayamizu, Tokyo (JP); Satoru Toyama, Tokyo (JP); Kota Mizuno, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/572,823

(22) PCT Filed: Jul. 17, 2015

(86) PCT No.: PCT/JP2015/070500
§ 371 (c)(1),
(2) Date: Nov. 9, 2017

(87) PCT Pub. No.: WO2017/013700
PCT Pub. Date: Jan. 26, 2017

(65) Prior Publication Data
US 2018/0143176 A1    May 24, 2018

(51) Int. Cl.
*G01N 33/28* (2006.01)
*H01F 27/00* (2006.01)
(Continued)

(52) U.S. Cl.
CPC ......... *G01N 33/2841* (2013.01); *G01R 31/00* (2013.01); *H01F 27/00* (2013.01); *H01F 27/004* (2013.01); *H01F 27/12* (2013.01)

(58) Field of Classification Search
None
See application file for complete search history.

(56) References Cited

U.S. PATENT DOCUMENTS

2013/0204827 A1* 8/2013 Kawachi ............ G01N 33/2841
706/46
2014/0036954 A1* 2/2014 Maity .................. G01J 5/0014
374/121

FOREIGN PATENT DOCUMENTS

JP         2004-200348 A        7/2004

OTHER PUBLICATIONS

International Search Report (PCT/ISA/210) dated Sep. 8, 2015, by the Japanese Patent Office as the International Searching Authority for International Application No. PCT/JP2015/070500.
(Continued)

*Primary Examiner* — Paul M. West
*Assistant Examiner* — Mark A Shabman
(74) *Attorney, Agent, or Firm* — Buchanan Ingersoll & Rooney PC (57) ABSTRACT

The present invention is a diagnosis method for internal fault of an oil-immersed electric apparatus using a silicone oil as an insulating oil. The method diagnoses an internal fault of the oil-immersed electric apparatus based on a first concentration ratio that is a concentration ratio between two gases selected from an analysis gas group consisting of hydrogen gas, methane gas, ethane gas, and ethylene gas contained in the, silicone oil, and a second concentration ratio that is a concentration ratio between the other two gases selected from the analysis gas group. A combination of the two gases and a combination of the other two gases are a combination of ethylene gas and hydrogen gas, a combination of ethane
(Continued)

gas and hydrogen gas, a combination of ethylene gas and methane gas, or a combination of methane gas and ethane gas.

5 Claims, 10 Drawing Sheets (51) Int. Cl.
*G01R 31/00* (2006.01)
*H01F 27/12* (2006.01)

(56) References Cited

OTHER PUBLICATIONS

Guideline for Power Transformer Refurbishment, Electric Technology Research Association, vol. 65, No. 1, Part II, Chapter 2, 2-2 to 2-5, Sep. 2009.
Office Action (Decision to Grant Patent) dated Dec. 15, 2015 in corresponding Japanese Application No. 2015-546756, with English translation.

* cited by examiner

DIAGNOSIS METHOD FOR INTERNAL FAULT OF OIL-IMMERSED ELECTRIC APPARATUS

TECHNICAL FIELD

The present invention relates to a diagnosis method for internal fault of an oil-immersed electric apparatus.

BACKGROUND ART

For example, a silicone oil, having a high flash point and a high level of safety compared with a mineral oil, may be used as an insulating oil in an on-board (e.g., railway) oil-immersed electric apparatus (e.g., transformer) with an emphasis on safety.

For an oil-immersed electric apparatus using a mineral oil as an insulating oil, a conventionally known method diagnoses an internal fault such as abnormal overheating using, for example, the types or concentrations of gas components of an insulating oil or the concentration ratios between a plurality of gas components of an insulating oil as indices, without stopping the apparatus.

For example, a known method divides a diagnosis map, where a horizontal axis represents a ratio between two gas components and a vertical axis represents a ratio between the other two gas components, into areas and then performs an abnormal diagnosis based on which area of the diagnosis map a plot corresponding to a measured value is placed in (for example, see Japanese Patent Laying-Open No. 2004-200348 (PTD 1)).

CITATION LIST

Patent Document

PTD 1: Japanese Patent Laying-Open No. 2004-200348

SUMMARY OF INVENTION

Technical Problem

However, no method has been studied in which an internal fault diagnosis is performed for an oil-immersed electric apparatus using a silicone oil. Since the silicone oil differs from the mineral oil in composition, for example, the types and concentrations of gas components of the silicone oil that are generated at an internal fault occurrence such as an abnormal discharge or abnormal overheating, or the concentration ratios between a plurality of such gas components differ from those of the mineral oil. It is thus inappropriate to use the diagnosis method for internal fault of an oil-immersed electric apparatus using a mineral oil for an internal fault diagnosis of an oil-immersed electric apparatus using a silicone oil without any change.

Specifically, although a ratio to an acetylene gas having high measurement sensitivity is used in PTD 1, the components of the silicone oil are resistant to degradation (have a high heat resistance), so that little or no acetylene gas, which is normally generated at the final stage of the degradation, is generated. For this reason, an internal fault diagnosis needs to be performed using a ratio between gas components that have measurement sensitivity lower than that of the acetylene gas, which may lead to lower diagnostic accuracy.

The present invention has been made in view of the above problem, and has an object to provide a diagnosis method for internal fault of an oil-immersed electric apparatus using a silicone oil as an insulating oil, which can diagnose the presence or absence of an internal fault occurrence for the oil-immersed electric apparatus with high accuracy using gas components of the silicone oil as indices.

Solution to Problem

The present invention is a diagnosis method for internal fault of an oil-immersed electric apparatus using a silicone oil as an insulating oil. The method diagnoses an internal fault of the oil-immersed electric apparatus based on a first concentration ratio that is a concentration ratio between two gases selected from an analysis gas group consisting of hydrogen gas, methane gas, ethane gas, and ethylene gas contained in the silicone oil, and a second concentration ratio that is a concentration ratio between the other two gases selected from the analysis gas group. A combination of the two gases and a combination of the other two gases are a combination of ethylene gas and hydrogen gas, a combination of ethane gas and hydrogen gas, a combination of ethylene gas and methane gas, or a combination of methane gas and ethane gas.

Advantageous Effects of Invention

The present invention can provide a diagnosis method for an oil-immersed electric apparatus using a silicone oil as an insulating oil, which can diagnose the presence or absence of an internal fault occurrence for the oil-immersed electric apparatus with high accuracy using the gas components of the silicone oil as indices.

DESCRIPTION OF EMBODIMENTS

An embodiment of the present invention will now be described with reference to the drawings. In the drawings, the same symbols or reference numerals represent the same or corresponding parts. In addition, a dimensional relationship, such as a length, width, thickness, and depth is appropriately changed for the sake of clarification and simplification of the drawings, and actual dimensional relationship is not represented.

Embodiment 1

An abnormal diagnosis method of the present embodiment is a method of diagnosing the presence or absence of an internal fault occurrence for an oil-immersed electric apparatus using a silicone oil as an insulating oil. A non-limiting example of the oil-immersed electric apparatus is an oil-immersed electric apparatus in which coil copper around which a piece of coil insulating paper is wound is disposed in a silicone oil. Specifically, such an apparatus is a transformer or the like. Since a silicone oil is frequently used in an on-board (e.g., railway) oil-immersed electric apparatus with emphasis on safety, the diagnosis method of the present embodiment can be preferably used for an on-board oil-immersed electric apparatus.

The analysis targets in the diagnosis method for internal fault of the present embodiment are four gases (hydrogen gas, methane gas, ethylene gas, and ethane gas) contained in a silicone oil. An internal fault diagnosis of an oil-immersed electric apparatus is performed based on a concentration ratio (first concentration ratio) between two gases selected from these four gases (analysis gas group) contained in the silicone oil and a concentration ratio (second concentration ratio) of the other two gases selected from the analysis gas group.

The combination of two gases and the combination of the other two gases are a combination of ethylene gas and hydrogen gas, a combination of ethane gas and hydrogen gas, a combination of ethylene gas and methane gas, or a combination of methane gas and ethane gas.

These are four combinations found to have a wide amount of change in gas component concentration ratio associated with a temperature rise of the silicone oil, through the study of the present inventors. An abnormal diagnosis performed based on the gas component concentration ratios of these combinations can reduce diagnostic errors, enabling a high-accuracy abnormal diagnosis.

The first concentration ratio and the second concentration ratio are preferably a concentration ratio of ethylene gas to hydrogen gas, a concentration ratio of ethane gas to hydrogen gas, a concentration ratio of ethylene gas to methane gas, or a concentration ratio of methane gas to ethane gas.

At least any one of the first concentration ratio and the second concentration ratio is preferably a concentration ratio of ethylene gas to hydrogen gas or a concentration ratio of ethane gas to hydrogen gas. More preferably, the first concentration ratio and the second concentration ratio are a concentration ratio of ethylene gas to hydrogen gas and a concentration ratio of ethane gas to hydrogen gas.

As a specific diagnosis method, a diagnosis map, where a horizontal axis represents a first component ratio and a vertical axis represents a second component ratio, is divided into areas (see FIG. 2 or 3 described in Example), and then, an internal fault diagnosis is performed based on which area of the diagnosis map the plots corresponding to the measured values of the first component ratio and second component ratio are placed in.

In the creation of a diagnosis map, for example, a test system simulating abnormal overheating of an oil-immersed electric apparatus using a silicone oil is constructed, the silicone oil is heated, and then, the generation behavior of the gas dissolved in the silicone oil is investigated. A diagnosis map (overheating-temperature-estimation diagnosis map) can be created based on the investigation results (see FIG. 2 or 3 described in Example). Then, the results of the gas-in-oil analysis of the silicone-oil-immersed electric apparatus can be applied to the overheating-temperature-estimation diagnosis map to estimate an overheating temperature (temperature estimation value) of the silicone-oil-immersed electric apparatus and to diagnose that an internal fault (abnormal overheating) has occurred when the temperature estimation value exceeds a predetermined threshold temperature.

Internal abnormalities in an oil-immersed electric apparatus using a mineral oil are conceivably a discharge and overheating. In particular, an acetylene gas generated by a discharge that may lead to a serious internal fault is an indicator gas that is important in the determination of an internal fault by a gas-in-oil analysis. However, the silicone oil is resistant to heat and is hard to generate an acetylene gas compared with the mineral oil, and accordingly, it is difficult to use an acetylene gas to diagnose an internal fault of an oil-immersed electric apparatus using a silicone oil. An internal fault can thus be determined based on four gases, namely, hydrogen gas, methane gas, ethylene gas, and ethane gas generated from a silicone oil in a wide range of temperatures.

The gas-in-oil concentration of a gas component generated due to an internal fault of a silicone-oil-immersed electric apparatus varies depending on an internal fault duration time and an area of an abnormal part, in addition to the temperature of the abnormal part, and thus, it is difficult to estimate an abnormal condition (overheating temperature) based on the gas-in-oil concentration alone. The concentration ratio between a plurality of gases in an oil, however, depends on the temperature of the abnormal part and does not depend on the internal fault duration time and the area of the abnormal part. It is therefore considered that the use of a concentration ratio between gas components may be effective at evaluating the temperature of an abnormal part.

To perform the diagnosis method of the present embodiment, first, a gas (sample gas) containing a dissolved gas in an insulating oil of the oil-immersed electric apparatus needs to be extracted. Non-limiting examples of the method of extracting a sample gas from an insulating oil include a method of stirring an oil in a well-closed chamber (or a well-closed oil-immersed electric apparatus) and taking out a sample gas volatilized toward the upper space (head space) of the well-closed chamber, a method of creating a vacuum of space in a space above an oil stored in a well-closed oil chamber and spraying the oil into the vacuum of space, and a method of bubbling an oil by an inert gas such as argon gas and extracting a sample gas.

To grasp the effects of the aging deterioration of internally coexisting materials and a silicone oil, materials to be used inside the oil-immersed electric apparatus may be investigated, or characteristics of the silicone oil may be measured as preliminary studies, together with a gas-in-oil analysis.

Although the present embodiment has described the case in which two indices are used, the diagnosis method of the present embodiment includes a diagnosis using an indicator gas in addition to these two indices. In an example case of using a total of three indices, a three-dimensional diagnosis map may be created, and an internal fault diagnosis may be performed based on the diagnosis map.

Gas Analyzer

Description will now be given of an example of a gas analyzer that can be used for analysis of gas components in the diagnosis method for internal fault of the present invention.

The gas analyzer mainly includes a gas passage through which a sample gas flows, and an optical detection system that detects light in a wavelength range including any wavelength of an absorption band of a measurement component.

The optical detection system includes, as its basic configuration, a gas cell connected to the passage, a light source that irradiates an analysis gas in the gas cell with light, and an optical detector that detects the light that has passed through the analysis gas. Alternatively, the optical detector may be a detector that detects not only the light that has passed through the analysis gas but also, for example, the light reflected off the analysis gas. A thermal conductivity detector (TCD), a flame ionization detector (FID), or any other detector can be used in place of the optical detector.

For example, the amount of change in optical transmittance due to the presence or absence of a gas component can be determined based on the intensity or the like of the light detected by the optical detector, thereby measuring the concentration of each gas component using, for example, a calibration curve preliminarily created.

The optical detection system optically analyzes the gas introduced into the gas cell provided at some midpoint of the gas passage. The gas to be introduced into the gas passage is normally a gas mixture of a sample gas taken out from an insulating oil and a carrier gas for introducing the sample gas into, for example, the gas cell. The carrier gas is not particularly limited but preferably may be the air in the atmosphere, because it can be supplied easily without the need for a supply of a special gas. Alternatively, the sample gas alone may be introduced into the gas passage without using the carrier gas.

To individually measure a plurality of types of gas components contained in the insulating oil (silicone oil), for example, a gas separation column can be used. In other words, the concentration of each gas component can be measured by causing a sample gas (e.g., a gas taken out from the upper space of a chamber storing an insulating oil in the oil-immersed electric apparatus) to flow through the gas separation column or the like and then introducing the sample gas into the gas cell or the like in the form of individual gas components separated physically or chemically. The gas separation column is an instrument that causes a sample gas to pass therethrough to separate individual measurement components with the use of a difference in transit time of each measurement component. The gas separation column may be various well-known separation columns used in the gas chromatography method or any other column, and is selected appropriately in accordance with the type of the measurement component to be analyzed.

Although the light source may be any light source that can emit light including an absorption band of a measurement component, in the case where the light corresponding to the absorption band of the measurement component is infrared light, it is preferably an infrared radiation source. The infrared light emitted from the infrared radiation source is more preferably mid-infrared light (wavelength: approximately 3 to 5 µm).

For example, when the sample gas contains a plurality of measurement components and the absorption bands of the measurement components are close to each other, only the light having a wavelength that does not overlap the absorption bands of the other measurement components needs to be detected to measure individual measurement components. For this purpose, an optical filter may be provided between the light source and the optical detector, which allows only the light having a desired wavelength range to pass therethrough and does not allow other light to pass therethrough. The light source may be a light source (narrow-band light source) that emits only the light in a desired wavelength range but does not emit other light. A non-limiting example of the narrow-band light source is an LED light source. For improved detection sensitivity, the wavelength of the light to be detected preferably includes a maximum absorption wavelength of the measurement component.

The method of analyzing a gas in an insulating oil may be (1) a method (online) of measuring a gas by an analyzer mounted in an oil-immersed electric apparatus (transformer), as well as (2) a method (offline) of taking out an insulating oil from a lower portion of an oil-immersed electric apparatus and performing measurements by an analyzer installed in another place (for example, see "*Denryokuyō Hennatsuki Kaisyū Gaidorainn*" [Guideline for Power Transformer Refurbishment], Electric Technology Research Association, Vol. 65, No.1, Part II, Chapter 2, 2-2 to 2-5). The analysis method (1) above is advantageous in that measurement results can be successively monitored online, leading to an early diagnosis of abnormal overheating. In general, however, the analysis method (2) above is widely used and can provide an analysis with higher sensitivity and higher accuracy.

EXAMPLES

Example 1

Figure 4:
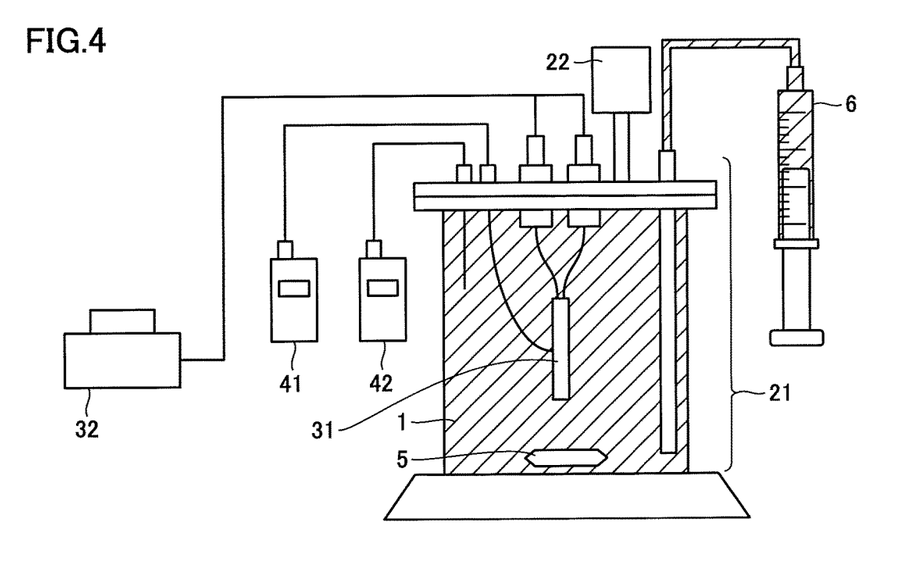
FIG. 4 is a schematic diagram of a test system simulating abnormal overheating of an oil-immersed electric apparatus using a silicone oil in Example 1.
Figure 5:
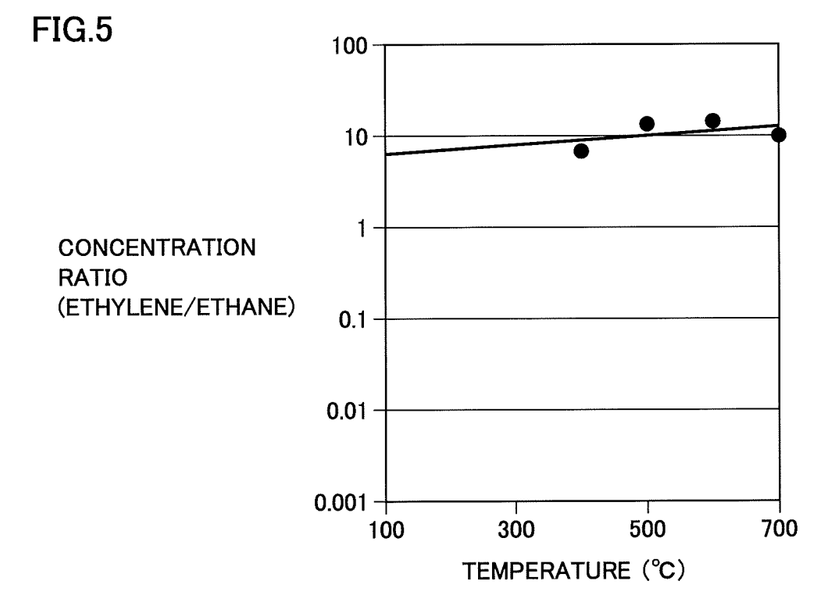
FIG. 5 is a graph showing a regression line obtained by the least squares method for the analysis results of the respective gas components shown in FIG. 1.
Figure 6:
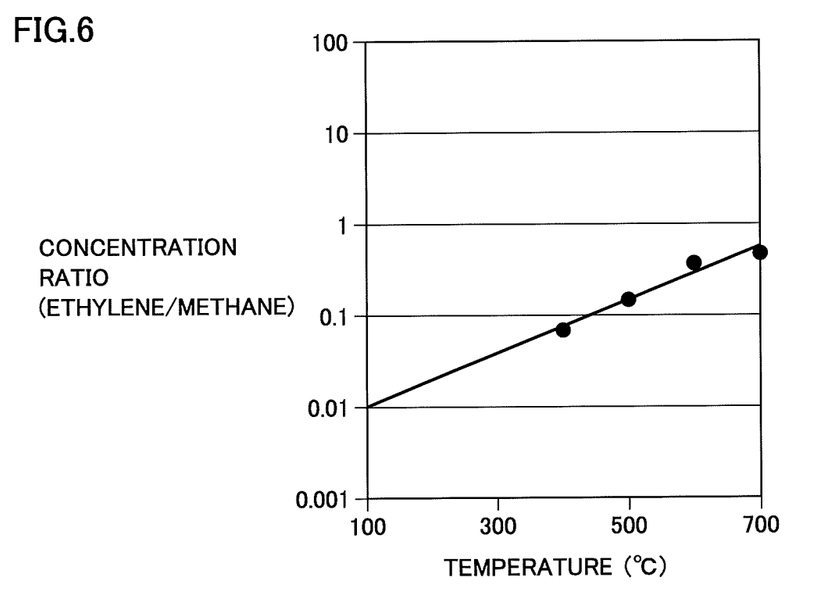
FIG. 6 is another graph showing a regression line obtained by the least squares method for the analysis results of the respective gas components shown in FIG. 1.
Figure 7:
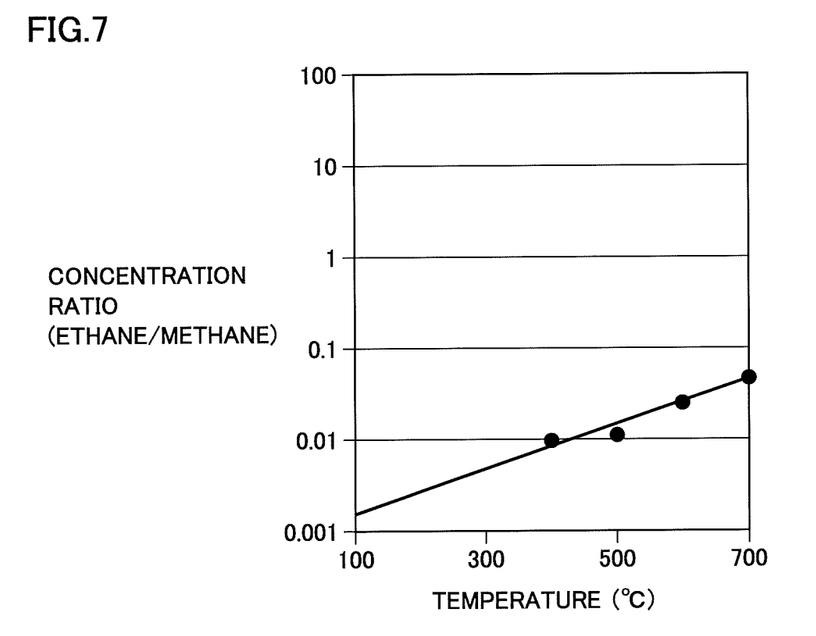
FIG. 7 is still another graph showing a regression line obtained by the least squares method for the analysis results of the respective gas components shown in FIG. 1.
Figure 8:
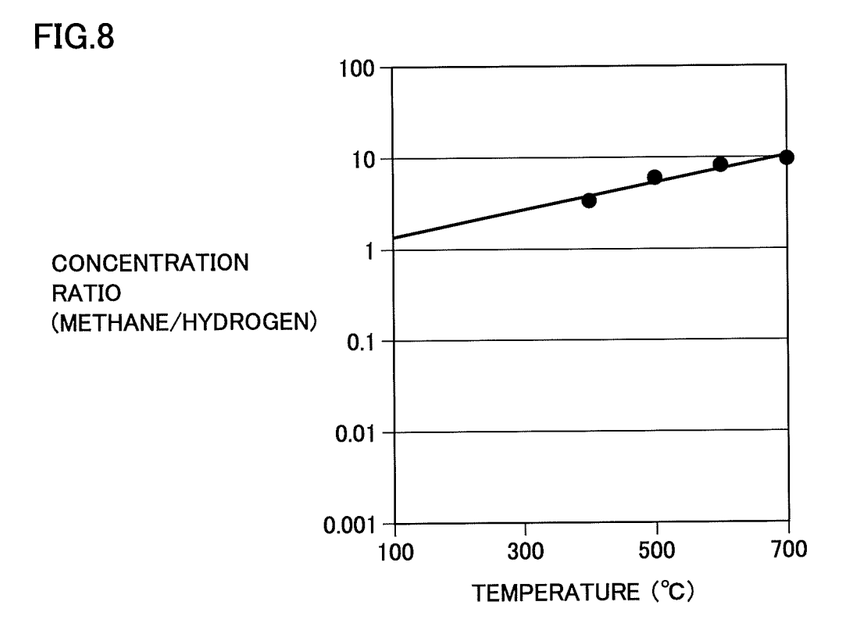
FIG. 8 is still another graph showing a regression line obtained by the least squares method for the analysis results of the respective gas components shown in FIG. 1.
Figure 9:
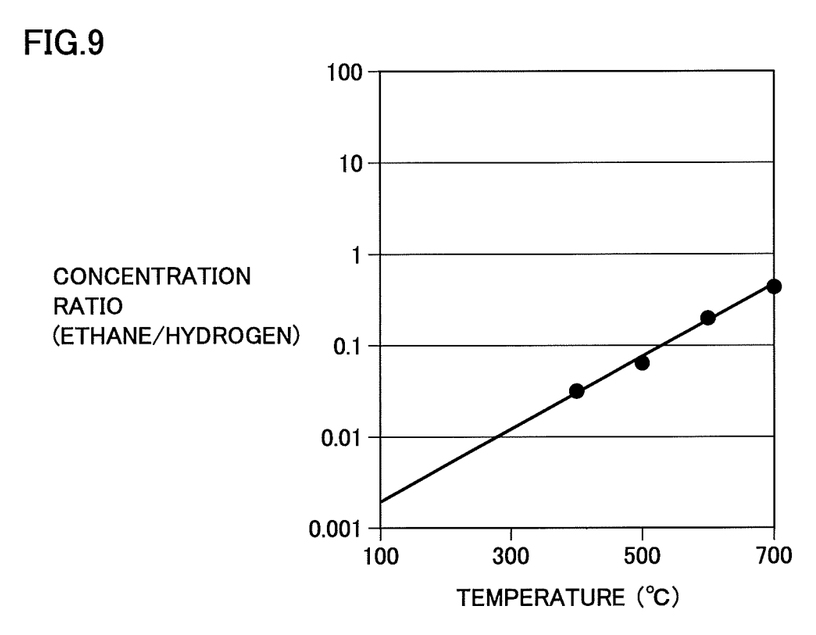
FIG. 9 is still another graph showing a regression line obtained by the least squares method for the analysis results of the respective gas components shown in FIG. 1.
Figure 10:
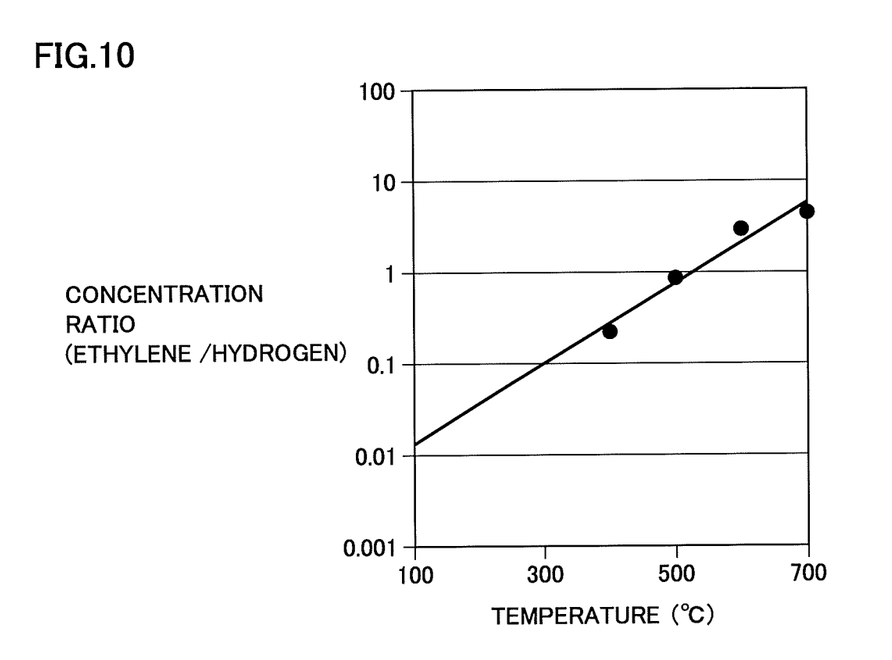
FIG. 10 is still another graph showing a regression line obtained by the least squares method for the analysis results of the respective gas components shown in FIG. 1.

To simulate a (locally) overheated state that occurs inside an oil-immersed electric apparatus using a silicone oil as an insulating oil, a heater 31 was installed inside a test vessel 21, and a silicone oil 1 was heated (see FIG. 4). Test vessel 21 is provided with a conservator 22, and heater 31 is supplied with power from an AC source 32.

The temperatures of heater 31 and silicone oil 1 were measured with a thermometer 41 and a thermometer 42, respectively. Heating of heater 31 was controlled based on the measurements performed with thermometers 41 and 42 and was maintained such that the temperature of silicone oil 1 was 400° C., 500° C., 600° C., and 700° C. To uniformly dissolve the gas components generated through pyrolysis of the silicone oil, silicone oil 1 was stirred with a stir bar 5. After heating at each temperature for 10 minutes, silicone oil 1 was taken out with a detachable oil extraction syringe 6.

For the silicone oil that had been taken out, the gas components dissolved in the silicone oil were extracted through bubbling by an inert gas, and the extracted gas components were measured by a gas chromatogaphy apparatus including a detector (TCD) mounted thereon, thereby measuring the concentrations of four types of gas components (hydrogen gas, methane gas, ethane gas, and ethylene gas) contained in the silicone oil.

Figure 1:
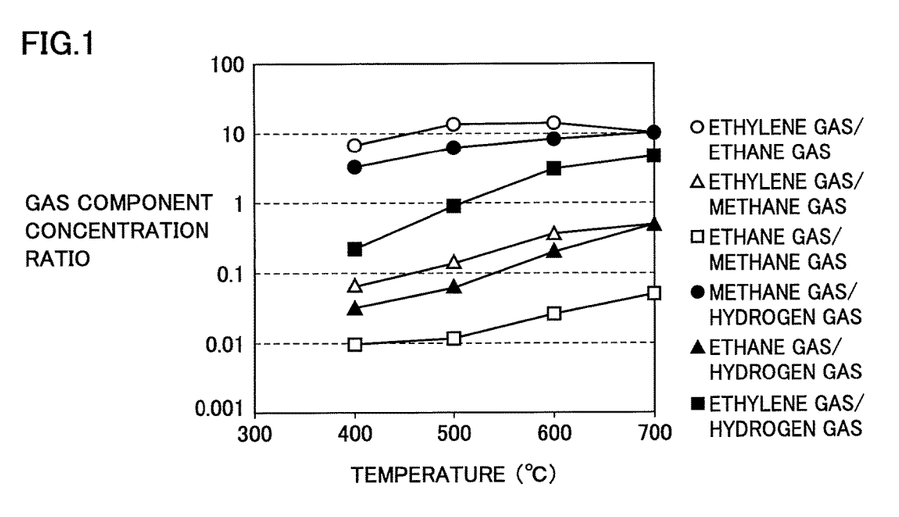
FIG. 1 is a graph showing analysis results of concentration ratios of gas components of a silicone oil in Example 1.

FIG. 1 shows the analysis results obtained by calculating the concentration ratios in combinations A to F of the gas components shown in Table 1 at the respective temperatures from the measured values of the concentrations of the respective gas components of the silicone oil. For the analysis results of the combinations of the respective gas components, FIGS. 5 to 10 show regression lines obtained by the least squares method, and Table 1 shows regression expressions thereof. In Table 1, k represents a constant k when a regression expression is represented as $y=ae^{kx}$ (e is the base of natural logarithms, and a and k are constants) and corresponds to a slope when the y-axis is represented logarithmically as in FIGS. 5 to 10.

TABLE 1

| Combination of gas components | Regression expression | k × 10000 |
|---|---|---|
| A: ethylene/ethane ($C_2H_4/C_2H_6$) | $y = 5.8\ e^{0.0011\ x}$ | 11 |
| B: ethylene/methane ($C_2H_4/CH_4$) | $y = 0.0050\ e^{0.0067\ x}$ | 67 |
| C: methane/ethane ($CH_4/C_2H_6$) | $y = 0.00087\ e^{0.0056\ x}$ | 56 |
| D: methane/hydrogen ($CH_4/H_2$) | $y = 0.95\ e^{0.0034\ x}$ | 34 |
| E: ethane/hydrogen ($C_2H_6/H_2$) | $y = 0.00084\ e^{0.0090\ x}$ | 90 |
| F: ethylene/hydrogen ($C_2H_4/H_2$) | $y = 0.0048\ e^{0.010\ x}$ | 100 |

The results shown in FIG. 1 and Table 1 reveal that there is a correlation between a gas component concentration ratio and a silicone oil temperature in the cases of (1) a combination of ethylene gas and hydrogen gas (ethylene gas/hydrogen gas: a concentration ratio of ethylene gas to hydrogen gas), (2) a combination of ethane gas and hydrogen gas (ethane gas/hydrogen gas: a concentration ratio of ethane gas to hydrogen gas), (3) a combination of ethylene gas and methane gas (ethylene gas/methane gas: a concentration ratio of ethylene gas to methane gas), and (4) a combination of methane gas and ethane gas (methane gas/ethane gas: a concentration ratio of methane gas to ethane gas).

The results also reveal that the amount of change in gas component concentration ratio with a temperature rise of the silicone oil increases in the order of (1) to (4) above ((1) has the greatest amount of change).

In the cases of (5) a combination of ethylene gas and ethane gas (ethylene gas/ethane gas: a concentration ratio of ethylene gas to ethane gas), and (6) a combination of methane gas and ethane gas (methane gas/ethane gas: a concentration ratio of methane gas to ethane gas, the amount of change in gas component concentration ratio with a temperature rise of the silicone oil was small compared with the combinations of two gases of (1) to (4) above. It is thus considered that the combinations (gas component ratios) of two gases of (5) and (6) above are not suitable for use in abnormal analysis of an oil-immersed electric apparatus using a silicone oil.

It is considered from the above results that a high-accuracy diagnosis is enabled by an abnormal diagnosis for an oil-immersed electric apparatus using a silicone oil, based on the combinations (gas component ratios) of two gases of (1) to (4) above.

Table 2 shows the measured values of the respective gas components that are the basis of the results of FIG. 1.

TABLE 2

| | Gas component concentration (ppm) | | | |
|---|---|---|---|---|
| Temperature (° C.) | $H_2$ | $CH_4$ | $C_2H_6$ | $C_2H_4$ |
| 400 | 91 | 305 | 3 | 21 |
| 500 | 194 | 1179 | 13 | 175 |
| 600 | 287 | 2374 | 60 | 867 |
| 700 | 335 | 3187 | 154 | 1535 |

Figure 2:
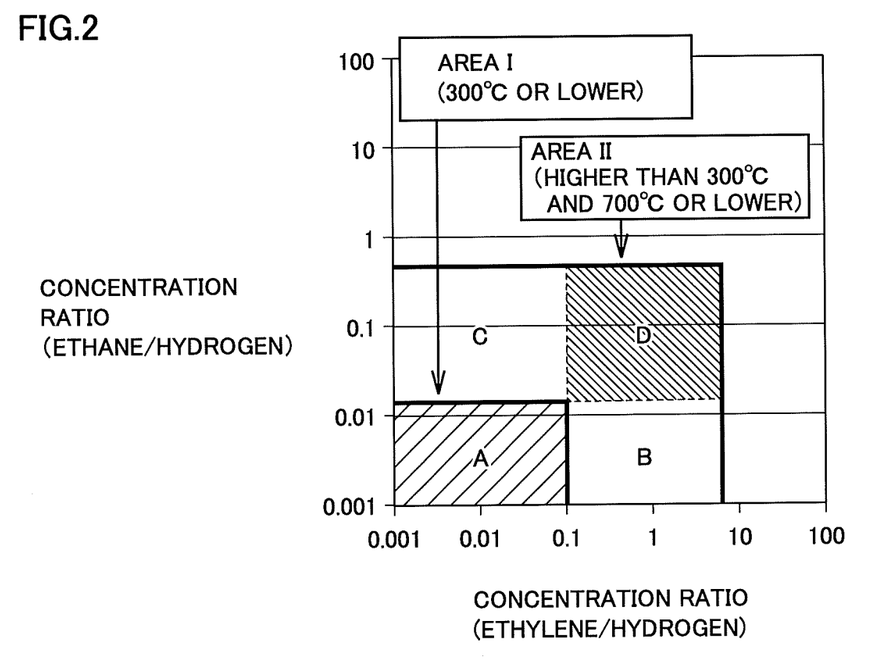
FIG. 2 shows an example of an overheating-temperature-estimation diagnosis map created based on the dependence of the gas component concentration ratios on temperature shown in FIG. 1.
Figure 3:
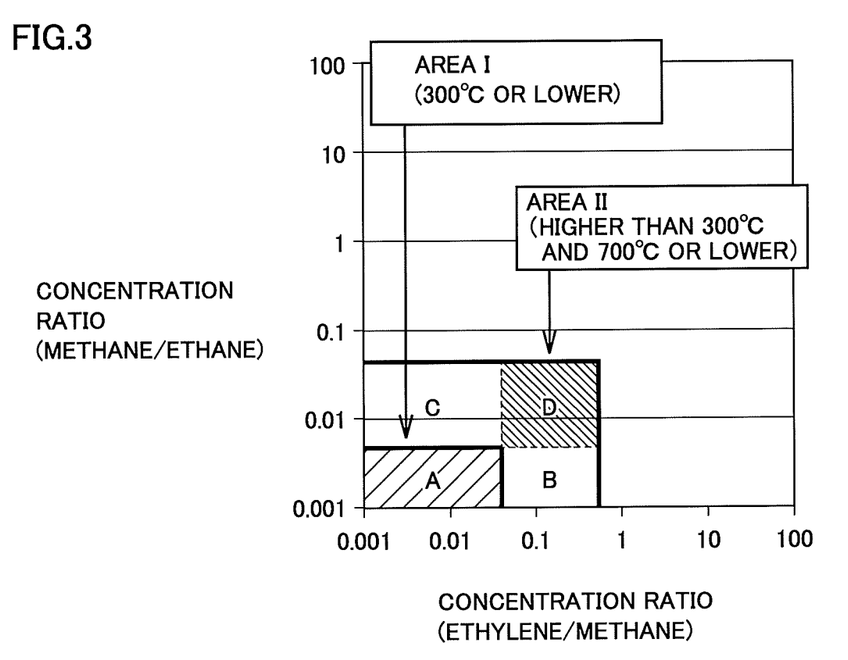
FIG. 3 is another example of an overheating-temperature-estimation diagnosis map created based on the dependence of the gas component concentration ratios on temperature shown in FIG. 1.

FIGS. 2 and 3 show examples of diagnosis maps (overheating-temperature-estimation diagnosis maps) created based on the dependence of the gas component ratios on temperature shown in FIG. 1. The diagnosis map of FIG. 2 was created based on the ethylene gas/hydrogen gas concentration ratio (horizontal axis) of (1) above and the ethane gas/hydrogen gas concentration ratio (vertical axis) of (2) above. The diagnosis map of FIG. 3 was created based on the ethylene gas/methane gas concentration ratio (horizontal axis) of (3) above and the methane gas/ethane gas concentration ratio (vertical axis) of (4) above.

In FIGS. 2 and 3, an area I (A) is an area corresponding to the concentration ratio between the gas components generated when the temperature of the silicone oil is 300° C. or lower, and an area II (B to D) is an area corresponding to the concentration ratio between the gas components generated when the temperature of the silicone oil is higher than 300° C. and 700° C. or lower.

It can be determined that abnormal overheating or the like has occurred when the concentration ratio between the respective gas components falls in "area D" of the area II. An internal fault occurrence can be determined more reliably than in the case where an internal fault occurrence is determined when the concentration ratio falls in the area II (any of the areas B to D).

As shown in FIG. 1, for the first concentration ratio and the second concentration ratio, the concentration ratio of ethylene gas to hydrogen gas (ethylene gas/hydrogen gas), the concentration ratio of ethane gas to hydrogen gas (ethane gas/hydrogen gas), the concentration ratio of ethylene gas to methane gas (ethylene gas/methane gas), or the concentration ratio of methane gas to ethane gas (methane gas/ethane gas) is preferably used as an indicator gas in abnormal analysis. Although the ratios obtained by reversing the numerators and denominators of the above-mentioned ratios can be used as indices of an abnormal diagnosis, the resultant ratios are inversely proportional to the temperature of the silicone oil, and accordingly, the scales of the diagnosis maps of FIGS. 2 and 3 are hard to see if they are not modified. For easily seeing the scales, the order of the scales of the diagnosis maps needs to be reversed, for example. The concentration ratios as shown in FIG. 1 are thus used conveniently as indices.

It is considered that for higher-accuracy diagnosis, an abnormal diagnosis is desirably performed using, as an indicator gas, the concentration ratio of ethylene gas to hydrogen gas (ethylene gas/hydrogen gas) or the concentration ratio of ethane gas to hydrogen gas (ethane gas/hydrogen gas) among the preferred concentration ratios above.

A diagnosis performed with the use of two indices (first concentration ratio and the second concentration ratio) selected from these indices increases a probability that an internal fault has occurred actually in the case where an internal fault occurrence is diagnosed compared with the case in which one indicator gas is used, resulting in a higher diagnostic accuracy.

In particular, it is considered that diagnostic accuracy can be increased when the first concentration ratio and the second concentration ratio are two gas component concentration ratios (the concentration ratio of ethylene gas to hydrogen gas and the concentration ratio of ethane gas to hydrogen gas) at which the amount of change with a temperature rise of the silicone oil is particularly large as shown in FIG. 2.

It is conceivable that the use of hydrogen gas as an indicator gas may not be desirable for an accurate diagnosis, because hydrogen gas can occur over time from, for example, a triazole derivative (Irgamet®) that is added to an insulating oil as an antioxidant, the internally coexistent materials of the oil-immersed electric apparatus. In such a case, an internal fault occurrence can be diagnosed with high accuracy by using the concentration ratios between the gas components excluding hydrogen gas (a concentration ratio of ethylene gas to methane gas, and a concentration ratio of methane gas to ethane gas) as the first concentration ratio and the second concentration ratio, as shown in FIG. 3, without using hydrogen gas as an indicator gas.

It should be understood that the embodiment disclosed herein is illustrative and non-restrictive in every respect. The scope of the present invention is defined by the scope of the claims, rather than the description above, and is intended to include any modifications within the scope and meaning equivalent to the scope of the claims.

REFERENCE SIGNS LIST 1 silicone oil, 21 test vessel, 22 conservator, 31 heater, 32 AC source, 41, 42 thermometer, 5 stir bar, 6 oil extraction syringe

The invention claimed is:

1. A diagnosis method for internal fault of an oil-immersed electric apparatus using a silicone oil as an insulating oil,
the method comprising diagnosing an internal fault of the oil-immersed electric apparatus based on a first concentration ratio that is a concentration ratio between two gases selected from an analysis gas group consisting of hydrogen gas, methane gas, ethane gas, and ethylene gas contained in the silicone oil, and a second concentration ratio that is a concentration ratio between the other two gases, which are not used for the first concentration ratio, selected from the analysis gas group,
a combination of the two gases and a combination of the other two gases being a combination of ethylene gas and hydrogen gas, a combination of ethane gas and hydrogen gas, a combination of ethylene gas and methane gas, or a combination of methane gas and ethane gas,
wherein a diagnosis map with a horizontal axis representing concentration ratios between the two gases and a vertical axis representing concentration ratios between the other two gases, each as a function of a temperature of the silicone oil, the diagnosis map being divided into area I and area II, and an internal fault diagnosis of the oil-immersed electric apparatus is performed based on which area of the diagnosis map a position corresponding to the first concentration ratio and the second concentration ratio is placed in, and
area I is an area corresponding to both concentration ratios between the two gases generated when the temperature of the silicone oil is 300° C. or lower and concentration ratios between the other two gases generated when the temperature of the silicone oil is 300° C. or lower, and area II is an area corresponding to concentration ratios between the two gases generated when the temperature of the silicone oil is higher than 300° C. and 700° C. or lower and/or concentration ratios between the other two gases generated when the temperature of the silicone oil is higher than 300° C. and 700° C. or lower.

2. The diagnosis method for internal fault according to claim 1, wherein the first concentration ratio and the second concentration ratio are a concentration ratio of ethylene gas to hydrogen gas, a concentration ratio of ethane gas to hydrogen gas, a concentration ratio of ethylene gas to methane gas, or a concentration ratio of methane gas to ethane gas.

3. The diagnosis method for internal fault according to claim 2, wherein at least any one of the first concentration ratio and the second concentration ratio is the concentration ratio of ethylene gas to hydrogen gas or the concentration ratio of ethane gas to hydrogen gas.

4. The diagnosis method for internal fault according to claim 3, wherein the first concentration ratio and the second concentration ratio are the concentration ratio of ethylene gas to hydrogen gas and the concentration ratio of ethane gas to hydrogen gas.

5. A diagnosis method for internal fault of an oil-immersed electric apparatus using a silicone oil as an insulating oil, the method comprising:
(i) determining a first concentration ratio that is a concentration ratio between two gases selected from an analysis gas group consisting of hydrogen gas, methane gas, ethane gas, and ethylene gas contained in the silicone oil, and a second concentration ratio that is a concentration ratio between the other two gases, which are not used for the first concentration ratio, selected from the analysis gas group,
a combination of the two gases and a combination of the other two gases being a combination of ethylene gas and hydrogen gas, a combination of ethane gas and hydrogen gas, a combination of ethylene gas and methane gas, or a combination of methane gas and ethane gas,
(ii) determining, on a diagnosis map, a position corresponding to the first concentration ratio and the second concentration ratio,
wherein the diagnosis map has a horizontal axis representing concentration ratios between the two gases and a vertical axis representing concentration ratios between the other two gases, each as a function of a temperature of the silicone oil, the diagnosis map being divided into area I and area II,
area I is an area corresponding to both concentration ratios between the two gases generated when the temperature of the silicone oil is 300° C. or lower and concentration ratios between the other two gases generated when the temperature of the silicone oil is 300° C. or lower, and area II is an area corresponding to concentration ratios between the two gases generated when the temperature of the silicone oil is higher than 300°C. and 700° C. or lower and/or concentration ratios between the other two gases generated when the temperature of the silicone oil is higher than 300° C. and 700° C. or lower,
(iii) diagnosing an internal fault of the oil-immersed electric apparatus when the determined position in step (ii) falls in the area II.

* * * * *